(12) United States Patent
Du (10) Patent No.: US 9,709,474 B2
(45) Date of Patent: Jul. 18, 2017

(54) AUTOMATIC MEASURING INSTRUMENT AND MEASURING METHOD FOR UNCONVENTIONAL NATURAL GAS CONTENT

(71) Applicants: PETRO CHINA CO. LTD SOUTHWEST OIL AND GAS FIELD EXPLORATION AND DEVELOPMENT RESEARCH INSTITUTE, Sichuan (CN); SOUTHWEST PETROLEUM UNIVERSITY, Sichuan (CN); SICHUAN KELITE OIL AND GAS TECHNOLOGY CO. LTD, Sichuan (CN)

(72) Inventor: Jian Du, Chengdu (CN)

(73) Assignee: PETRO CHINA CO., LTD. SOUTHWEST OIL AND GAS FIELD EXPLORATION AND DEVELOPMENT RESEARCH INSTITUTE, Chengdu, Sichuan (CN)

( * ) Notice: Subject to any disclaimer, the term of this patent is extended or adjusted under 35 U.S.C. 154(b) by 186 days.

(21) Appl. No.: 14/766,453

(22) PCT Filed: Oct. 16, 2013

(86) PCT No.: PCT/CN2013/085279
§ 371 (c)(1),
(2) Date: Aug. 6, 2015

(87) PCT Pub. No.: WO2014/121619
PCT Pub. Date: Aug. 14, 2014

(65) Prior Publication Data
US 2015/0369715 A1 Dec. 24, 2015

(30) Foreign Application Priority Data
Feb. 7, 2013 (CN) .......................... 2013 1 0049522

(51) Int. Cl.
*G01F 23/292* (2006.01)
*G01N 7/16* (2006.01)
(Continued)

(52) U.S. Cl.
CPC ............. *G01N 7/16* (2013.01); *G01F 23/292* (2013.01); *G01N 7/14* (2013.01); *G01N 33/241* (2013.01); *G01N 33/0016* (2013.01)

(58) Field of Classification Search
CPC ........ F04B 49/12; F04B 49/225; F04B 9/123; F04B 53/14; F04B 53/10; F04B 53/16;
(Continued)

(56) References Cited

U.S. PATENT DOCUMENTS 1,767,515 A * 6/1930 Davis ..................... F16N 13/02
184/27.1
2,372,302 A * 3/1945 Swindin .................. F04B 43/08
417/566

* cited by examiner

*Primary Examiner* — Tony Ko
(74) *Attorney, Agent, or Firm* — Raymond Y. Chan; David and Raymond Patent Firm (57) ABSTRACT

An automatic measuring instrument for an unconventional natural gas content includes a parsing tank, a thermostatic water bath box, a gas collection measuring cylinder, a balance measuring cylinder, a liquid storage tank, a data acquisition and control system, an upper computer, and a lifting device for driving the gas collection measuring cylinder and the balance measuring cylinder to move relative to the liquid storage tank, wherein both the lower ports of the gas collection measuring cylinder and the balance measuring cylinder are placed below the liquid level of the liquid storage tank. The parsing tank is placed in the thermostatic water bath box. A gas guide tube A is connected to the parsing tank and the gas collection measuring cylinder. A gas guide tube B is connected to the balance measuring cylinder and the outside atmosphere is fed therein. By the adoption (Continued)

of the measuring instrument, the constant-pressure isasteric automatic continuous measurement of the content of natural gas contained in an unconventional natural gas reservoir sample is achieved. Moreover, the measuring instrument is simple in structure, reliable in measurement and analysis results, convenient in operation and high in measurement accuracy.

9 Claims, 2 Drawing Sheets

(51) Int. Cl.
*G01N 7/14* (2006.01)
*G01N 33/24* (2006.01)
*G01N 33/00* (2006.01)

(58) Field of Classification Search
CPC .......... F04B 19/22; F04B 15/02; F04B 9/125; F16N 13/04; F16N 13/02
See application file for complete search history.

AUTOMATIC MEASURING INSTRUMENT AND MEASURING METHOD FOR UNCONVENTIONAL NATURAL GAS CONTENT

CROSS REFERENCE OF RELATED APPLICATION

This is a U.S. National Stage under 35 U.S.C. 371 of the International Application Number PCT/CN2013/085279, filed Oct. 16, 2013, which claims priority under 35 U.S.C. 119(a-d) to Chinese application number 201310049522.6, filed Feb. 7, 2013.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to a measuring device for natural gas content, and more particularly to an automatic measuring instrument and a measuring method for an unconventional natural gas content.

Description of Related Arts

At present, the measurement of the content of natural gas contained in a natural gas reservoir sample at home and abroad means to collect the content of natural gas contained in a given weight of sample placed in a sample parsing tank (namely a constant-volume airtight container) within a specified measurement time under the conditions of certain temperature (stimulated reservoir temperature) and pressure (generally atmospheric pressure). A tiny-pressure sensor gas content volume measurement method and a gas flowmeter measurement method are mainly adopted at home and abroad. The tiny-pressure sensor gas content volume measurement method lies in that tiny pressure generated when the natural gas enters an airtight measuring tube from the parsing tank is increased to make the liquid level in the measuring tube begin to drop from an upper limit value. The measurement of the natural gas content just means to read and record a volume value corresponding to a scale change value after the liquid level in the measuring tube drops to a lower limit value, and in the meantime, the vertical height (namely one end, connected to the atmosphere, of a U-shaped tube) of a liquid storage balance tube needs to be manually changed in order to keep the liquid level in the measuring tube to be consistent to the liquid level in the liquid storage balance tube (namely the tiny pressure difference is zero), so as to ensure the measurement accuracy of the gas content. A gas exhaust valve of the parsing tank is closed. A gas exhaust valve of the measuring tube is opened and the height of the liquid storage tube is adjusted to enable the liquid level in the measuring tube and the liquid level in the liquid storage tube to reach the upper limit values again. The gas exhaust valve of the measuring tube is closed and the gas exhaust valve of the parsing tank is opened again, and then next constant-volume measurement of gas content can be started. The tiny-pressure sensor gas volume measurement method needs real-time observation and record by manpower. It is large in manual operation and reading errors and high in labor intensity, and instruments are not easy to carry because of larger size, whereas the gas flowmeter measurement method means to directly connect a gas flowmeter to an outlet of the sample parsing tank to measure and automatically record the content of the natural gas separated out from the sample. The measurement accuracy of this method depends on the selected flowmeter and will be influenced since the content of the parsed natural gas contained in the reservoir sample is not flowing in a continuous constant-flow manner.

Unconventional natural gases, such as shale gas and coal bed gas, are important constituents of the world energy sources. With the continuous rise of world energy consumption, the unconventional natural gas energy sources, such as shale gas and coal bed gas, get more and more attention, and a development technology thereof is developed fast thereupon. In order to ensure the validity and reliability of results in calculation of development reserves of the unconventional natural gas and to reduce the manual operation error and alleviate the labor intensity of test work, there is a need for a novel instrument which can be used for directly and accurately measuring the content of natural gas (parsed or adsorbed natural gas) of an unconventional natural gas reservoir sample in a downhole temperature environment and has a function of continuous automatic constant-volume measurement for long-term and non-constant-flow gas output.

SUMMARY OF THE PRESENT INVENTION

The invention aims at providing an automatic measuring instrument and a measuring method which are simple in structure, convenient to operate and capable of automatically measuring the content of the unconventional natural gas contained in a reservoir sample under a simulated oil gas downhole temperature against the defects of an existing technology.

The purpose of the present invention is realized by means of the following technical solutions: an automatic measuring instrument for a unconventional natural gas content comprising a parsing tank, a thermostatic water bath box, a gas collection measuring cylinder, a balance measuring cylinder, a liquid storage tank, a data acquisition and control system, and an upper computer. The lower end of the gas collection measuring cylinder is open and the upper end thereof is sealed by a sealing cover A. A floating sheet A is arranged in the gas collection measuring cylinder. The lower end of the balance measuring cylinder is open and the upper end thereof is sealed by a sealing cover B. A floating sheet B is arranged in the gas collection measuring cylinder. Both the lower ports of the gas collection measuring cylinder and the balance measuring cylinder are placed below the liquid level of the liquid storage tank. The parsing tank is placed in the thermostatic water bath box and consists of a tank body and a sealing cover C. A temperature transmitter is arranged on the sealing cover C. A photoelectric liquid level sensor A is arranged on the sealing cover A. A photoelectric liquid level sensor B is arranged on the sealing cover B. A gas guide tube A is connected to the internal space of the parsing tank and the internal space of the gas collection measuring cylinder. A gas guide tube B is connected to the internal space of the balance measuring cylinder and external atmosphere. A normally-opened electromagnetic valve is arranged on the gas guide tube A. The gas guide tube A is also connected with an evacuation branch gas tube which is equipped with a normally-closed electromagnetic valve. The temperature transmitter, the photoelectric liquid level sensor A, the photoelectric liquid level sensor B, the normally-opened electromagnetic valve, the normally-closed electromagnetic valve, and a driving device of a lifting device are electrically connected with the data acquisition and control system respectively. The data acquisition and control system is electrically connected with the upper computer.

The invention also comprises a lifting device for driving the gas collection measuring cylinder and the balance measuring cylinder to move relative to the liquid storage tank up and down.

The upper computer is an industrial touch screen or computer with an embedded system.

A protecting cap is also arranged on the lower end of the gas collection measuring cylinder and the lower end of the balance measuring cylinder, respectively, and an axial through hole is formed in the middle of each protection cap, wherein the hole diameter of each through hole is smaller than the outer diameter of the floating sheet A and the outer diameter of the floating sheet B.

The lifting device comprises a driving device, a worm wheel and worm mechanism, a screw rod, and a support, wherein the worm and worm mechanism comprises a worm wheel and a worm which are meshed to each other. The driving device is a motor which is horizontally arranged, wherein an output shaft of the motor is connected with the worm through a transmission device. The screw rod is vertically arranged. The worm wheel is sheathed on the screw rod and is fixedly connected with the screw rod. The support is fixedly arranged on the liquid storage tank. In addition, the support and the screw rod are assembled into a whole through threads and the motor is electrically connected with the data acquisition and control system.

The lifting device comprises a driving device, a worm wheel and worm mechanism, a screw rod, and a support, wherein the worm wheel and worm mechanism comprises a worm wheel and a worm which are meshed to each other. The driving device is a motor which is horizontally arranged, wherein an output shaft of the motor is connected with the worm through a transmission device. The screw rod is vertically arranged. The worm wheel is sheathed on the screw rod and is fixedly connected with the screw rod. Both the gas collection measuring cylinder and the balance measuring cylinder are fixedly arranged on the support. The support and the screw rod are assembled into a whole through threads and the motor is electrically connected with the data acquisition and control system.

The motor is a stepping motor or a linear motor.

A water drain valve is arranged at the bottom of the water storage tank.

A measuring method adopting the automatic measuring instrument for the unconventional natural gas content comprises the following steps:

S1. configuring equipment before measurement, wherein an upper computer controls the normally-closed electromagnetic valve to be opened and the normally-opened electromagnetic valve to be closed through the data acquisition and control system, controls the driving device of the lifting device to drive the liquid storage tank to ascend so as to drive the liquid level in the gas collection measuring cylinder and the liquid level in the balance measuring cylinder to raise or drive the gas collection measuring cylinder and the balance measuring cylinder to descend, wherein the photoelectric liquid level sensor A and the photoelectric liquid level sensor B transmit liquid level parameters to the data acquisition and control system in real time, wherein the data acquisition and control system transmits the acquired parameters to the upper computer, and when the liquid level in the gas collection measuring cylinder and the liquid level in the balance measuring cylinder reach a set upper limit, the upper computer controls the driving device of the lifting device to stop working, the normally-closed electromagnetic valve to be closed and the normally-opened electromagnetic valve to be opened;

S2. placing an unconventional natural gas reservoir sample in the parsing tank and putting the parsing tank into the thermostatic water bath box, wherein the temperature in the thermostatic water bath tank is measured by the temperature transmitter, the temperature transmitter transmits temperature parameters to the data acquisition and control system, and the data acquisition and control system transmits the acquired parameters to the upper computer;

S3. measuring the gas content, wherein the natural gas is continuously separated out from the reservoir sample under a simulated downhole temperature environment and then enters the gas collection measuring cylinder through the gas guide tube A and the normally-opened electromagnetic valve, so that the liquid level in the gas collection measuring cylinder drops, and meanwhile, the liquid level in the balance measuring cylinder and the liquid level in the liquid storage tank raise thereupon, and both floating sheets in the gas collection measuring cylinder and the balance measuring cylinder move along with the liquid level change, wherein the photoelectric liquid level sensor A and the photoelectric liquid level sensor B transmit the liquid level parameters to the data acquisition and control system in real time, wherein the data acquisition and control system transmits the acquired parameters to the upper computer, and the upper computer controls the lifting device to drive the liquid storage tank to descend or drive the gas collection measuring cylinder and the balance measuring cylinder to ascend according to the measured liquid level difference between the gas collection measuring cylinder and the balance measuring cylinder, so that the liquid level in the balance measuring cylinder gradually drops; when detecting that the difference of the liquid level in the gas collection measuring cylinder and the liquid level in the balance measuring cylinder is less than a set accuracy, wherein the upper computer controls the driving device of the lifting device to stop working, and the gas pressure in the gas collection measuring cylinder is equal to the external atmospheric pressure again, wherein when the liquid level in the gas collection measuring cylinder reaches a preset lower limit, the normally-opened electromagnetic valve is closed, and when the upper computer controls the driving device of the lifting device to stop working, namely the gas pressure in the gas collection measuring cylinder being equal to the external atmospheric pressure, the corresponding measuring cylinder volume difference, relative to an original liquid level, of the liquid level of the gas collection measuring cylinder at this moment is the gas output of the sample, wherein upper computer finishes once gas content measurement according to the measured and recorded change value of the liquid level in the gas collection measuring cylinder, wherein after once gas content measurement is finished, the upper computer controls the normally-closed electromagnetic valve to be opened and the normally-opened electromagnetic valve to be closed through the data acquisition and control system, and then controls the driving device of the lifting device to drive the liquid storage tank to ascend or drive the gas collection measuring cylinder and the balance measuring cylinder to descend, so that the liquid level in the gas collection measuring cylinder and the liquid level in the balance measuring cylinder raise, wherein when the liquid level in the gas collection measuring cylinder and the liquid level in the balance measuring cylinder reach a set upper limit, the upper computer controls the driving device of the lifting device to stop working, the normally-closed electromagnetic valve to be closed and the normally-opened electromagnetic valve to be opened, and then second measurement can be started;

S4. repeating the step S3 till the natural gas is stopped to be separated out from the reservoir sample or a set measurement time is reached; and S5. carrying out accumulated calculation automatically by the upper computer to obtain the total gas content of the reservoir sample.

The present invention has the advantages that: the present invention relates to an instrument capable of accurately measuring the content of the natural gas contained in unconventional natural gas reservoir samples (shale, coal and the like) under a simulated oil gas downhole temperature environment, which realizes constant-pressure isasteric automatic continuous measurement of the content of the natural gas contained in the unconventional natural gas reservoir samples according to an isobaric liquid level balance principle that the liquid level of liquid (for instance, water) in a U-shaped communicating tube is constant in height under the same atmospheric pressure condition by adopting a photoelectric non-contact closed-loop measurement and control method.

The measurement result of the present invention is not affected by manual reading and operation errors (or measurement lag caused by the sensitivity of the tiny-pressure sensor) caused by surface tension of the inner wall of the gas collection measuring cylinder, and compared with an existing measuring device. The present invention is simple in structure, reliable in measurement and analysis results, and simple in procedure operation of a touch screen. It has the measurement accuracy far higher than that of the tiny-pressure sensor measurement method and the gas flowmeter measurement method used at present. It can save a large amount of human resource cost in field testing and can be used in a laboratory or fields, such as well drilling.

The present invention creatively proposes and implements the solutions. The two photoelectric liquid level sensors are used to respectively measure the height changes of the liquid levels in the gas collection measuring cylinder and the balance measuring cylinder which are used for constant-volume measurement of the natural gas. The mechanisms, such as the motor, can be controlled and adjusted according to the measured value of the liquid level height difference of the two measuring cylinders through a data acquisition and control program of the computer. The worm wheel and worm mechanism, and the like are used to adjust the positions of the gas collection measuring cylinder and the balance measuring cylinder relative to the liquid storage tank, and accordingly, once more balance of the liquid levels of the two measuring cylinders and the gas content measurement can be realized and this constant-volume testing process is repeated till the measurement of the natural gas content of the reservoir sample is finished. A photoelectric sensing technology, closed-loop measurement and control of the liquid levels in the measuring cylinders, and a computer software technology are comprehensively used for measurement of the content of the natural gas contained in the unconventional reservoir sample, and thus a non-contact measuring method and an instrument device which have a practical value is realized. The present invention can be used for measuring the content of the natural gas contained in multiple natural reservoir samples, such as shale and coal. The present invention also can be used for continuous constant-volume measurement of related gas volumes in other industrial fields (such as mining, chemical engineering, environmental protection, food and medicines).

These and other objectives, features, and advantages of the present invention will become apparent from the following detailed description, the accompanying drawings, and the appended claims.

BRIEF DESCRIPTION OF THE DRAWINGS

In Figures, the parsing tank 1, the thermostatic water bath box 2, the gas collection measuring cylinder 3, the balance measuring cylinder 4, the liquid storage tank 5, the data acquisition and control system 6, the upper computer 7, the sealing cover A 8, the floating sheet A 9, the sealing cover B 10, the floating sheet B 11, the lifting device 12, the tank body 13, the sealing cover C 14, the temperature transmitter 15, the photoelectric liquid level sensor A 16, the photoelectric liquid level sensor B 17, the gas guide tube A 18, the gas guide tube B 19, the normally-opened electromagnetic valve 20, the evacuation branch gas tube 21, the normally-closed electromagnetic valve 22, the protecting cap 23, the water drain valve 24, the driving device 25, the worm wheel and worm mechanism 26, the screw rod 27, and the support 28 are illustrated.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

The present invention will be further described as below in conjunction with the embodiments and attached drawings, and the protection scope of the present invention is not limited to the following statements:

Embodiment 1

Figure 1:
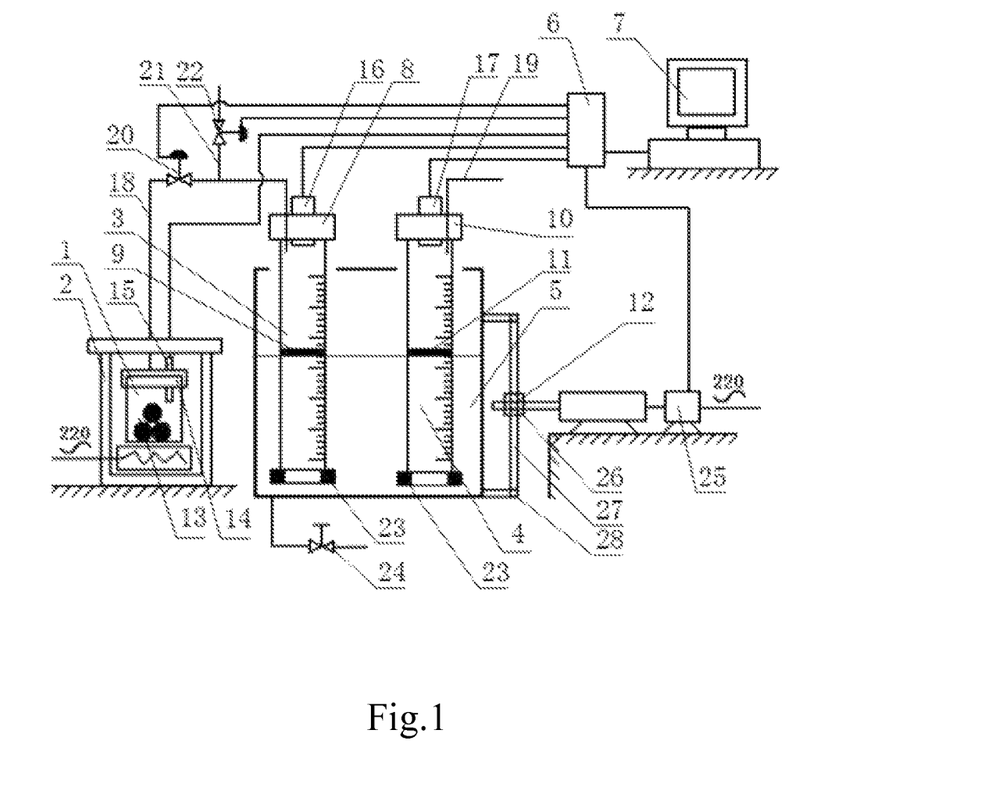
FIG. 1 is a structural schematic diagram of the present invention.

As shown in FIG. 1, an automatic measuring instrument for a unconventional natural gas content comprises a parsing tank 1, a thermostatic water bath box 2, a gas collection measuring cylinder 3, a balance measuring cylinder 4, a liquid storage tank 5, a data acquisition and control system 6, and an upper computer 7. The lower end of the gas collection measuring cylinder 3 is open and the upper end thereof is sealed by a sealing cover A 8. A floating sheet A 9 is arranged in the gas collection measuring cylinder 3. The lower end of the balance measuring cylinder 4 is open and the upper end thereof is sealed by a sealing cover B 10. A floating sheet B 11 is arranged in the gas collection measuring cylinder 3. Both the lower ports of the gas collection measuring cylinder 3 and the balance measuring cylinder 4 are placed below the liquid level of the liquid storage tank 5. The liquid storage tank 5 is also connected with a lifting device for driving the liquid storage tank 5 to move up and down; the parsing tank 1 is placed in the thermostatic water bath box 2 and consists of a tank body 13 and a sealing cover C 14. A temperature transmitter 15 is arranged on the sealing cover C 14. A photoelectric liquid level sensor A 16 is arranged on the sealing cover A 8. A photoelectric liquid level sensor B 17 is arranged on the sealing cover B 10. A gas guide tube A 18 is connected to the internal space of the parsing tank 1 and the internal space of the gas collection measuring cylinder 3. A gas guide tube B 19 is connected to the internal space of the balance measuring cylinder 4 and external atmosphere. A normally-opened electromagnetic valve 20 is arranged on the gas guide tube A 18. The gas guide tube A 18 is also connected with an evacuation branch gas tube 21 which is equipped with a normally-closed electromagnetic valve 22. The temperature transmitter 15, the photoelectric liquid level sensor A 16, the photoelectric liquid level sensor B 17, the normally-opened electromagnetic valve 20, the normally-closed electromagnetic valve 22, and a driving device 25 of the lifting device 12 are electrically connected with the data acquisition and control system 6 respectively. The data acquisition and control system 6 is electrically connected with the upper computer 7.

The upper computer 7 is an industrial touch screen or a computer provided with an embedded system.

A protecting cap 23 is also arranged on the lower end of the gas collection measuring cylinder 3 and the lower end of the balance measuring cylinder 4, respectively, an axial through hole. The hole diameter of which is smaller than the outer diameter of the floating sheet A 9. The outer diameter of the floating sheet B 11 is formed in the middle of each protecting cap 23, and the protecting caps 23 can be used to prevent the floating sheets in the gas collection measuring cylinder 3 and the balance measuring cylinder 4 from missing.

The lifting device 12 comprises a driving device 25, a worm wheel and worm mechanism 26, a screw rod 27, and a support 28. The worm wheel and worm mechanism 26 comprises a worm wheel and a worm which are meshed to each other. The driving device 25 is a motor which is horizontally arranged. An output shaft of the motor is connected with the worm through a transmission device. The screw rod is vertically arranged. The worm wheel is sheathed on the screw rod 27 and is fixedly connected with the screw rod 27. The support 28 is fixedly arranged on the liquid storage tank 5, and the support 28 and the screw rod are assembled into a whole through threads. The motor is electrically connected with the data acquisition and control system 6. The motor drives the worm to rotate forwards or backwards. The worm drives the screw rod to rotate through the worm wheel, so that the liquid storage tank 5 on which the support 28 is fixed moves correspondingly up or down. The transmission device is a coupling or a speed reducer.

The motor is a stepping motor or a linear motor.

A water drain valve 24 is arranged on the bottom of the water storage tank and is used for draining water in the liquid storage tank off in a process of transporting the instrument so as to ensure the transportation safety of the instrument.

The measuring method adopting the automatic measuring instrument for the unconventional natural gas content comprises the following steps:

S1. configuring equipment before measurement, the upper computer 7 controlling the normally-closed electromagnetic valve 22 to be opened and the normally-opened electromagnetic valve 20 to be closed through the data acquisition and control system 6, controlling the driving device 25 of the lifting device 12 to drive the liquid storage tank 5 to ascend so as to drive the liquid level in the gas collection measuring cylinder 3 and the liquid level in the balance measuring cylinder 4 to raise, the photoelectric liquid level sensor A 16 and the photoelectric liquid level sensor B 17 transmitting liquid level parameters to the data acquisition and control system 6 in real time, the data acquisition and control system 6 transmitting the acquired parameters to the upper computer 7, when the liquid level in the gas collection measuring cylinder 3 and the liquid level in the balance measuring cylinder 4 reach a set upper limit, the upper computer 7 controlling the driving device 25 of the lifting device 12 to stop working, the normally-closed electromagnetic valve 22 to be closed and the normally-opened electromagnetic valve 20 to be opened;

S2. placing the unconventional natural gas reservoir sample in the parsing tank 1 and putting the parsing tank 1 into the thermostatic water bath box 2, the temperature in the thermostatic water bath tank 2 being measured by the temperature transmitter 15, the temperature transmitter 15 transmitting temperature parameters to the data acquisition and control system 6, and the data acquisition and control system 6 transmitting the acquired parameters to the upper computer 7;

S3. measuring the gas content, the natural gas being continuously separated out from the reservoir sample under a simulated downhole temperature environment and then entering the gas collection measuring cylinder 3 through the gas guide tube A 18 and the normally-opened electromagnetic valve 20, so that the liquid level in the gas collection measuring cylinder 3 drops, and meanwhile, the liquid level in the balance measuring cylinder 4 and the liquid level in the liquid storage tank 5 raise thereupon, both the floating sheets in the gas collection measuring cylinder 3 and the balance measuring cylinder 4 moving along with the liquid level change, the photoelectric liquid level sensor A 16 and the photoelectric liquid level sensor B 17 transmitting the liquid level parameters to the data acquisition and control system 6 in real time, the data acquisition and control system 6 transmitting the acquired parameters to the upper computer 7, the upper computer 7 controlling the driving device 25 of the lifting device 12 to drive the liquid storage tank 5 to descend according to the measured liquid level difference between the gas collection measuring cylinder 3 and the balance measuring cylinder 4, since the gas collection measuring cylinder 3 and the balance measuring cylinder 4 are fixed, the liquid level in the balance measuring cylinder 4 gradually dropping with the descending of the liquid storage tank 5, when detecting that the difference of the liquid level in the gas collection measuring cylinder 3 and the liquid level in the balance measuring cylinder 4 is less than a set accuracy, the upper computer 7 controlling the driving device 25 of the lifting device 12 to stop working, the gas pressure in the gas collection measuring cylinder 3 being equal to the external atmospheric pressure again, when the liquid level in the gas collection measuring cylinder 3 reaches a preset lower limit, the normally-opened electromagnetic valve 20 being closed, when the upper computer 7 controls the driving device 25 of the lifting device 12 stops working, namely the gas pressure in the gas collection measuring cylinder 3 being equal to the external atmospheric pressure, the corresponding measuring cylinder volume difference, relative to an original liquid level, namely the change value of the liquid level upper limit value, of the liquid level of the gas collection measuring cylinder 3 at this moment being the gas output of the reservoir sample, the upper computer 7 finishing once gas content measurement according to the measured and recorded change value of the liquid level in the gas collection measuring cylinder 3, after once gas content measurement is finished, the upper computer 7 controlling the normally-closed electromagnetic valve 22 to be opened and the normally-opened electromagnetic valve 20 to be closed through the data acquisition and control system 6, and then controlling the driving device 25 of the lifting device 12 to drive the liquid storage tank 5 to ascend, so that the liquid level in the gas collection measuring cylinder 3 and the liquid level in the balance measuring cylinder 4 raise, when the liquid level in the gas collection measuring cylinder 3 and the liquid level in the balance measuring cylinder 4 reach a set upper limit value, the upper computer 7 controlling the driving device 25 of the lifting device 12 to stop working, the normally-closed electromagnetic valve 22 to be closed and the normally-opened electromagnetic valve 20 to be opened, and then second measurement can be started;

S4. repeating the step S3 till the natural gas being stopped to be separated out from the reservoir sample or a set measurement time being reached; and S5. carrying out accumulated calculation automatically through the upper computer 7 to obtain the total gas content of the reservoir sample, and other various analysis, graph display, data transmission and the like being also carried out as required.

Embodiment 2

Figure 2:
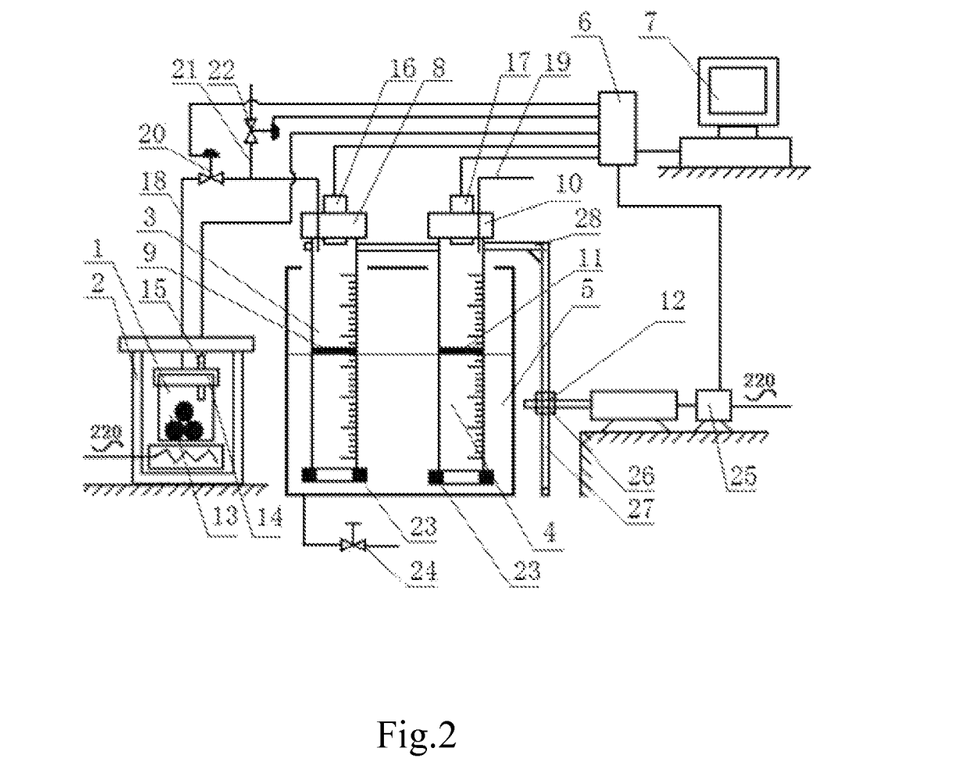
FIG. 2 is another structural schematic diagram of the present invention.

As shown in FIG. 2, an automatic measuring instrument for a unconventional natural gas content comprises a parsing tank 1, a thermostatic water bath box 2, a gas collection measuring cylinder 3, a balance measuring cylinder 4, a liquid storage tank 5, a data acquisition and control system 6, and an upper computer 7. The lower end of the gas collection measuring cylinder 3 is open and the upper end thereof is sealed by a sealing cover A 8. A floating sheet A 9 is arranged in the gas collection measuring cylinder 3. The lower end of the balance measuring cylinder 4 is open and the upper end thereof is sealed by a sealing cover B 10. A floating sheet B 11 is arranged in the gas collection measuring cylinder 3. Both the lower ports of the gas collection measuring cylinder 3 and the balance measuring cylinder 4 are placed below the liquid level of the liquid storage tank 5. The gas collection measuring cylinder 3 and the balance measuring cylinder 4 are also connected with a lifting device 12 for driving the gas collection measuring cylinder 3 and the balance measuring cylinder 4 to move up and down. The parsing tank 1 is placed in the thermostatic water bath box 2 and consists of a tank body 13 and a sealing cover C 14. A temperature transmitter 15 is arranged on the sealing cover C 14. A photoelectric liquid level sensor A 16 is arranged on the sealing cover A 8. A photoelectric liquid level sensor B 17 is arranged on the sealing cover B 10. A gas guide tube A 18 is connected to the internal space of the parsing tank 1 and the internal space of the gas collection measuring cylinder 3. A gas guide tube B 19 is connected to the internal space of the balance measuring cylinder 4 and external atmosphere. A normally-opened electromagnetic valve 20 is arranged on the gas guide tube A 18. The gas guide tube A 18 is also connected with an evacuation branch gas tube 21 which is equipped with a normally-closed electromagnetic valve 22. The temperature transmitter 15, the photoelectric liquid level sensor A 16, the photoelectric liquid level sensor B 17, the normally-opened electromagnetic valve 20, the normally-closed electromagnetic valve 22, and a driving device 25 of the lifting device 12 are electrically connected with the data acquisition and control system 6 respectively. The data acquisition and control system 6 is electrically connected with the upper computer 7.

The upper computer 7 is an industrial touch screen or a computer provided with an embedded system.

A protecting cap 23 is also arranged on the lower end of the gas collection measuring cylinder 3 and the lower end of the balance measuring cylinder 4 respectively, an axial through hole. The hole diameter of which is smaller than the outer diameter of the floating sheet A 9. The outer diameter of the floating sheet B 11 is formed in the middle of each protecting cap 23, and the protecting caps 23 can be used to prevent the floating sheets in the gas collection measuring cylinder 3 and the balance measuring cylinder 4 from missing.

The lifting device 12 comprises a driving device 25, a worm wheel and worm mechanism 26, a screw rod 27, and a support 28. The worm wheel and worm mechanism 26 comprises a worm wheel and a worm which are meshed to each other. The driving device 25 is a motor which is horizontally arranged. An output shaft of the motor is connected with the worm through a transmission device. The screw rod is vertically arranged. The worm wheel is sheathed on the screw rod 27 and is fixedly connected with the screw rod 27. The gas collection measuring cylinder 3 and the balance measuring cylinder 4 are fixedly arranged on the support 28. The support 28 and the screw rod are assembled into a whole through threads. The motor is electrically connected with the data acquisition and control system 6. The motor drives the worm to rotate forwards or backwards. The worm drives the screw rod to rotate through the worm wheel, so that the gas collection measuring cylinder 3 and the balance measuring cylinder 4 which are fixedly connected with the support 28 move correspondingly up or down. The transmission device is a coupling or a speed reducer.

The motor is a stepping motor or a linear motor.

A water drain valve 24 is arranged on the bottom of the water storage tank and is used for draining water in the liquid storage tank 5 off in a process of transporting the instrument so as to ensure the transportation safety of the instrument.

The measuring method adopting the automatic measuring instrument for the unconventional natural gas content comprises the following steps:

S1. configuring equipment before measurement, the upper computer 7 controlling the normally-closed electromagnetic valve 22 to be opened and the normally-opened electromagnetic valve 20 to be closed through the data acquisition and control system 6, controlling the driving device 25 of the lifting device 12 to drive the liquid storage tank 5 to ascend so as to drive the liquid level in the gas collection measuring cylinder 3 and the liquid level in the balance measuring cylinder 4 to raise, the photoelectric liquid level sensor A 16 and the photoelectric liquid level sensor B 17 transmitting liquid level parameters to the data acquisition and control system 6 in real time, the data acquisition and control system 6 transmitting the acquired parameters to the upper computer 7, when the liquid level in the gas collection measuring cylinder 3 and the liquid level in the balance measuring cylinder 4 reach a preset upper limit value, the upper computer 7 controlling the driving device 25 of the lifting device 12 to stop working, the normally-closed electromagnetic valve 22 to be closed and the normally-opened electromagnetic valve 20 to be opened;

S2. placing the unconventional natural gas reservoir sample in the parsing tank 1 and putting the parsing tank 1 into the thermostatic water bath box 2, the temperature in the thermostatic water bath tank 2 being measured by the temperature transmitter 15, the temperature transmitter 15 transmitting temperature parameters to the data acquisition and control system 6, and the data acquisition and control system 6 transmitting the acquired parameters to the upper computer 7;

S3. measuring the gas content, the natural gas being continuously separated out from the reservoir sample under a simulated downhole temperature environment and then entering the gas collection measuring cylinder 3 through the gas guide tube A 18 and the normally-opened electromagnetic valve 20, so that the liquid level in the gas collection measuring cylinder 3 drops, and meanwhile, the liquid level in the balance measuring cylinder 4 and the liquid level in the liquid storage tank 5 raise thereupon, both the floating sheets in the gas collection measuring cylinder 3 and the balance measuring cylinder 4 moving along with the liquid level change, the photoelectric liquid level sensor A 16 and the photoelectric liquid level sensor B 17 transmitting the liquid level parameters to the data acquisition and control system 6 in real time, the data acquisition and control system 6 transmitting the acquired parameters to the upper computer 7, the upper computer 7 controlling the driving device 25 of the lifting device 12 to drive the gas collection measuring cylinder 3 and the balance measuring cylinder 4 to ascend according to the measured liquid level difference between the gas collection measuring cylinder 3 and the balance measuring cylinder 4, since the liquid storage tank 5 is fixed, the liquid level in the balance measuring cylinder 4 gradually dropping with the ascending of the gas collection measuring cylinder 3 and the balance measuring cylinder 4, when detecting that the difference of the liquid level in the gas collection measuring cylinder 3 and the liquid level in the balance measuring cylinder 4 is less than a set accuracy, the upper computer 7 controlling the driving device 25 of the lifting device 12 to stop working, the gas pressure in the gas collection measuring cylinder 3 being equal to the external atmospheric pressure again, when the liquid level in the gas collection measuring cylinder 3 reaches a preset lower limit, the normally-opened electromagnetic valve 20 being closed, when the upper computer 7 controls the driving device 25 of the lifting device 12 stops working, namely the gas pressure in the gas collection measuring cylinder 3 being equal to the external atmospheric pressure, the corresponding measuring cylinder volume difference, relative to an original liquid level, namely the change value of the liquid level upper limit value, of the liquid level of the gas collection measuring cylinder 3 at this moment being the gas output of the reservoir sample, the upper computer 7 finishing once gas content measurement according to the measured and recorded change value of the liquid level in the gas collection measuring cylinder 3, after once gas content measurement is finished, the upper computer 7 controlling the normally-closed electromagnetic valve 22 to be opened and the normally-opened electromagnetic valve 20 to be closed through the data acquisition and control system 6, and then controlling the driving device 25 of the lifting device 12 to drive the gas collection measuring cylinder 3 and the balance measuring cylinder 4 to descend, so that the liquid level in the gas collection measuring cylinder 3 and the liquid level in the balance measuring cylinder 4 raise, when the liquid level in the gas collection measuring cylinder 3 and the liquid level in the balance measuring cylinder 4 reach a set upper limit value, the upper computer 7 controlling the driving device 25 of the lifting device 12 to stop working, the normally-closed electromagnetic valve 22 to be closed and the normally-opened electromagnetic valve 20 to be opened, and then second measurement can be started;

S4. repeating the step S3 till the natural gas being stopped to be separated out from the reservoir sample or a set measurement time being reached; and S5. carrying out accumulated calculation automatically by the upper computer 7 to obtain the total gas content of the reservoir sample, and other various analysis, graph display, data transmission and the like being also carried out as required.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An automatic measuring instrument for an unconventional natural gas content, comprising:

a parsing tank, a thermostatic water bath box, a gas collection measuring cylinder, a balance measuring cylinder, a liquid storage tank, a data acquisition and control system and an upper computer, wherein the lower end of the gas collection measuring cylinder is open and the upper end thereof is sealed by a first sealing cover, wherein a first floating sheet is arranged in the gas collection measuring cylinder, wherein the lower end of the balance measuring cylinder is open and the upper end thereof is sealed by a second sealing cover, wherein a second floating sheet is arranged in the gas collection measuring cylinder, wherein both the lower ports of the gas collection measuring cylinder and the balance measuring cylinder are placed below the liquid level of the liquid storage tank, wherein the parsing tank is placed in the thermostatic water bath box and includes a tank body and a third sealing cover, wherein a temperature transmitter is arranged on the third sealing cover, wherein a first photoelectric liquid level sensor is arranged on the first sealing cover, wherein a second photoelectric liquid level sensor is arranged on the second sealing cover, wherein a first gas guide tube is connected to the internal space of the parsing tank and the internal space of the gas collection measuring cylinder, wherein a second gas guide tube is connected to the internal space of the balance measuring cylinder and external atmosphere, wherein a normally-opened electromagnetic valve is arranged on the first gas guide tube, wherein the first gas guide tube is also connected with an evacuation branch gas tube which is equipped with a normally-closed electromagnetic valve, wherein the temperature transmitter, the first photoelectric liquid level sensor, the second photoelectric liquid level sensor, the normally-opened electromagnetic valve, a normally-closed electromagnetic valve, and a driving device of a lifting device are electrically connected with the data acquisition and control system respectively, wherein the data acquisition and control system is electrically connected with the upper computer; and a lifting device driving the gas collection measuring cylinder and the balance measuring cylinder to move up and down relative to the liquid storage tank.

2. The automatic measuring instrument for the unconventional natural gas content according to claim 1, wherein the upper computer is an industrial touch screen or a computer provided with an embedded system.

3. The automatic measuring instrument for the unconventional natural gas content according to claim 1, wherein a protecting cap is also arranged at the lower end of the gas collection measuring cylinder and the lower end of the balance measuring cylinder respectively, and an axial through hole is formed in the middle of each protecting cap, wherein the hole diameter of each of the through holes is smaller than the outer diameter of the first floating sheet and the outer diameter of the second floating sheet.

4. The automatic measuring instrument for the unconventional natural gas content according to claim 1, wherein the lifting device comprises a driving device, a worm wheel and worm mechanism, a screw rod and a support, wherein the worm wheel and worm mechanism comprises a worm wheel and a worm which are meshed to each other; the driving device is a motor which is horizontally arranged, wherein an output shaft of the motor is connected with the worm through a transmission device; the screw rod is vertically arranged; the worm wheel is sheathed on the screw rod and is fixedly connected with the screw rod; the support is fixed on the liquid storage tank, and the support and the screw rod are assembled into a whole through threads; and the motor is electrically connected with the data acquisition and control system.

5. The automatic measuring instrument for the unconventional natural gas content according to claim 1, wherein the lifting device comprises a driving device, a worm wheel and worm mechanism, a screw rod and a support, wherein the worm wheel and worm mechanism comprises a worm wheel and a worm which are meshed to each other; the driving device is a motor which is horizontally arranged, wherein an output shaft of the motor is connected with the worm through a transmission device; the screw rod is vertically arranged; the worm wheel is sheathed on the screw rod and is fixedly connected with the screw rod; the gas collection measuring cylinder and the balance measuring cylinder are fixed on the support, and the support and the screw rod are assembled into a whole through threads; and the motor is electrically connected with the data acquisition and control system.

6. The automatic measuring instrument for the unconventional natural gas content according to claim 4 or 5, wherein the motor is a stepping motor or a linear motor.

7. The automatic measuring instrument for the unconventional natural gas content according to claim 1, wherein a water drain valve is arranged at the bottom of the water storage tank.

8. A measuring method adopting the automatic measuring instrument for the unconventional natural gas content according to claim 1, comprising the steps of:

(S1) configuring equipment before measurement, the upper computer controlling the normally-closed electromagnetic valve to be opened and the normally-opened electromagnetic valve to be closed through the data acquisition and control system, controlling the driving device of the lifting device to drive the liquid storage tank to ascend or drive the gas collection measuring cylinder and the balance measuring cylinder to descend, so that the liquid level in the gas collection measuring cylinder and the liquid level in the balance measuring cylinder raise, the first photoelectric liquid level sensor and the second photoelectric liquid level sensor transmitting liquid level parameters to the data acquisition and control system in real time, the data acquisition and control system transmitting the acquired parameters to the upper computer, when the liquid level in the gas collection measuring cylinder and the liquid level in the balance measuring cylinder reach a set upper limit value, the upper computer controlling the driving device of the lifting device to stop working, the normally-closed electromagnetic valve to be closed and the normally-opened electromagnetic valve to be opened;

(S2) placing the unconventional natural gas reservoir sample in the parsing tank and putting the parsing tank into the thermostatic water bath box, the temperature in the thermostatic water bath box being measured by the temperature transmitter, the temperature transmitter transmitting temperature parameters to the data acquisition and control system, and the data acquisition and control system transmitting the acquired parameters to the upper computer;

(S3) measuring the gas content, the natural gas being continuously separated out from the reservoir sample under a simulated downhole temperature environment and then entering the gas collection measuring cylinder through the first gas guide tube and the normally-opened electromagnetic valve, so that the liquid level in the gas collection measuring cylinder drops, and meanwhile, the liquid level in the balance measuring cylinder and the liquid level in the liquid storage tank raise thereupon, both the floating sheets in the gas collection measuring cylinder and the balance measuring cylinder moving along with the liquid level change, the first photoelectric liquid level sensor and the second photoelectric liquid level sensor transmitting the liquid level parameters to the data acquisition and control system in real time, the data acquisition and control system transmitting the acquired parameters to the upper computer, the upper computer controlling the driving device of the lifting device to drive the liquid storage tank to descend, or drive the gas collection measuring cylinder and the balance measuring cylinder to ascend according to the measured liquid level difference between the gas collection measuring cylinder and the balance measuring cylinder, so that the liquid level in the balance measuring cylinder gradually dropping; when detecting that the difference of the liquid level in the gas collection measuring cylinder and the liquid level in the balance measuring cylinder being less than a set accuracy, the upper computer controlling the driving device of the lifting device to stop working, the gas pressure in the gas collection measuring cylinder being equal to the external atmospheric pressure again; when the liquid level in the gas collection measuring cylinder reaching a preset lower limit, the normally-opened electromagnetic valve being closed, and when the upper computer controlling the driving device of the lifting device stops working, namely the gas pressure in the gas collection measuring cylinder being equal to the external atmospheric pressure, the corresponding measuring cylinder volume difference, relative to an original liquid level, of the liquid level of the gas collection measuring cylinder at this moment being the gas output of the sample, the upper computer finishing once gas content measurement according to the measured and recorded change value of the liquid level in the gas collection measuring cylinder, after once gas content measurement being finished, the upper computer controlling the normally-closed electromagnetic valve to be opened and the normally-opened electromagnetic valve to be closed through the data acquisition and control system, and then controlling the driving device of the lifting device to drive the liquid storage tank to ascend, or drive the gas collection measuring cylinder and the balance measuring cylinder to descend, so that the liquid level in the gas collection measuring cylinder and the liquid level in the balance measuring cylinder raise, and when the liquid level in the gas collection measuring cylinder and the liquid level in the balance measuring cylinder reaching a set upper limit value, the upper computer controlling the driving device of the lifting device to stop working, the normally-closed electromagnetic valve to be closed and the normally-opened electromagnetic valve to be opened, and then second measurement can be started;

(S4) repeating the step S3 till the natural gas being stopped to be separated out from the reservoir sample or a set measurement time being reached; and (S5) carrying out accumulated calculation automatically by the upper computer to obtain the total gas content of the reservoir sample.

9. The automatic measuring instrument for the unconventional natural gas content according to claim 5, wherein said motor is a stepping motor or a linear motor.

\* \* \* \* \*